United States Patent
Tung et al.

(10) Patent No.: US 8,247,366 B2
(45) Date of Patent: *Aug. 21, 2012

(54) AZEOTROPE-LIKE COMPOSITIONS OF 1,1,2,3-TETRACHLOROPROPENE AND HYDROGEN FLUORIDE

(75) Inventors: Hsueh S. Tung, Getzville, NY (US); Hang T. Pham, Amherst, NY (US); Rajiv R. Singh, Getzville, NY (US); Daniel C. Merkel, West Seneca, NY (US); Robert Johnson, Lancaster, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/198,162

(22) Filed: Aug. 4, 2011

(65) Prior Publication Data

US 2011/0287996 A1    Nov. 24, 2011

Related U.S. Application Data

(62) Division of application No. 12/607,802, filed on Oct. 28, 2009, now Pat. No. 8,008,243.

(60) Provisional application No. 61/110,227, filed on Oct. 31, 2008.

(51) Int. Cl.
*C11D 7/50* (2006.01)

(52) U.S. Cl. ........ 510/407; 510/408; 510/412; 510/415; 252/364

(58) Field of Classification Search .................. 510/407, 510/408, 412, 415; 252/364
See application file for complete search history.

(56) References Cited

U.S. PATENT DOCUMENTS

| | | | |
|---|---|---|---|
| 4,535,194 A | 8/1985 | Woodard | |
| 4,650,914 A | 3/1987 | Woodard | |
| 5,206,367 A | 4/1993 | Urban | |
| 5,811,603 A | 9/1998 | Elsheikh | |
| 5,811,605 A | 9/1998 | Tang et al. | |
| 5,877,359 A | 3/1999 | Elsheikh | |
| 5,969,198 A | 10/1999 | Thenappan et al. | |
| 6,013,846 A | 1/2000 | Wismer et al. | |
| 6,166,274 A | 12/2000 | Chen et al. | |
| 6,198,010 B1 | 3/2001 | Yoshikawa et al. | |
| 6,235,951 B1 | 5/2001 | Sakyu et al. | |
| 6,316,681 B1 | 11/2001 | Yoshikawa et al. | |
| 7,795,480 B2 | 9/2010 | Merkel et al. | |
| 8,008,243 B2 * | 8/2011 | Tung et al. | 510/407 |
| 2002/0143215 A1 | 10/2002 | Tung et al. | |
| 2005/0085674 A1 | 4/2005 | Nakada et al. | |
| 2005/0101810 A1 | 5/2005 | Owens et al. | |
| 2007/0007488 A1 | 1/2007 | Singh et al. | |
| 2009/0030244 A1 | 1/2009 | Merkel et al. | |
| 2009/0224207 A1 | 9/2009 | Pham et al. | |
| 2009/0227822 A1 | 9/2009 | Pham et al. | |
| 2009/0256110 A1 | 10/2009 | Merkel et al. | |
| 2009/0287027 A1 | 11/2009 | Merkel et al. | |
| 2010/0113322 A1 | 5/2010 | Tung et al. | |
| 2010/0185030 A1 | 7/2010 | Elsheikh et al. | |
| 2010/0191025 A1 | 7/2010 | Perdrieux | |
| 2011/0004035 A1 | 1/2011 | Merkel et al. | |

* cited by examiner

*Primary Examiner* — Gregory Webb
(74) *Attorney, Agent, or Firm* — Bruce O. Bradford

(57) ABSTRACT

An azeotrope-like composition consisting essentially of 1,1,2,3-tetrachloropropene and hydrogen fluoride is provided, as well as methods that involve such an azeotrope-like composition.

22 Claims, 1 Drawing Sheet

P-T-X OF TCP/HF SYSTEM

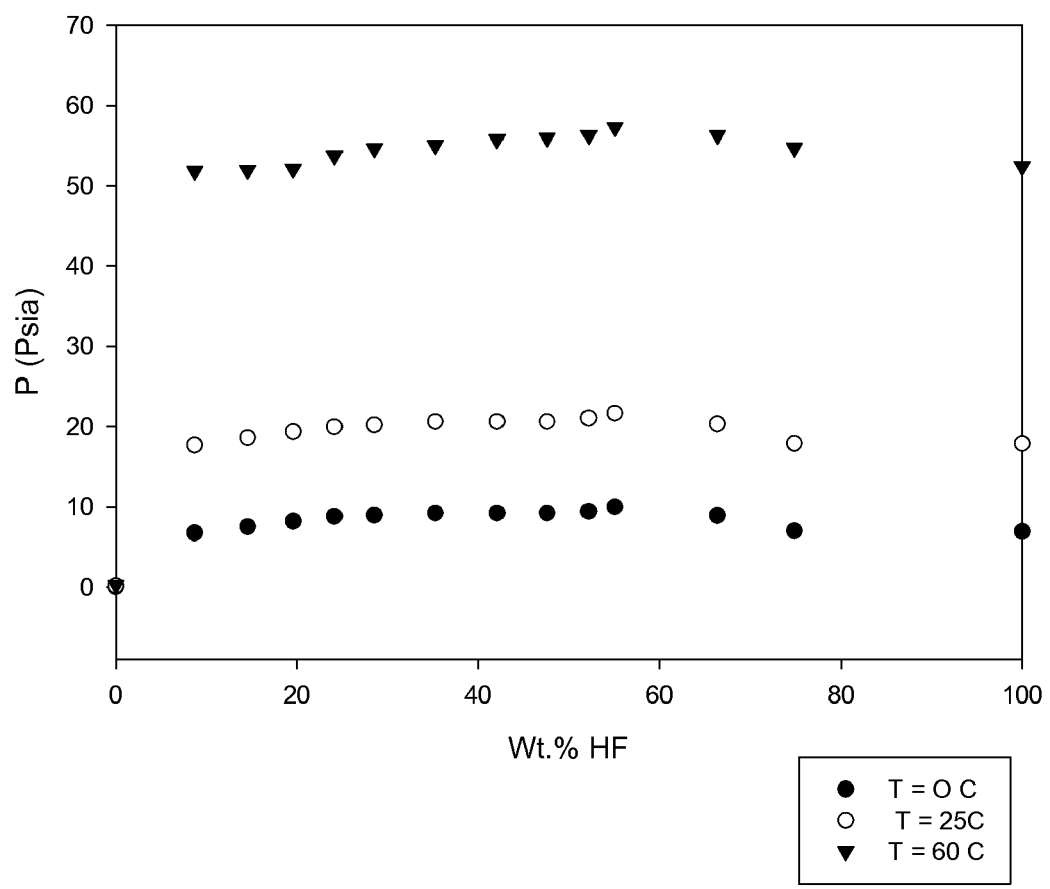

AZEOTROPE-LIKE COMPOSITIONS OF 1,1,2,3-TETRACHLOROPROPENE AND HYDROGEN FLUORIDE

CROSS-REFERENCE TO RELATED APPLICATIONS

This application is a Divisional of U.S. application Ser. No. 12/607,802, filed on Oct. 28, 2009 (now pending) which claims priority benefit of U.S. Provisional Application No. 61/110,227, filed Oct. 31, 2008, each of which is incorporated herein by reference.

BACKGROUND OF THE INVENTION

1. Field of Invention

The present invention is directed to azeotrope-like compositions. More particularly, the invention is directed to azeotrope-like compositions comprising a hydrofluoroolefin and hydrogen fluoride.

2. Description of the Prior Art

Many azeotropes possess properties that make them useful as solvents. For example, azeotropes have a constant boiling point that avoids boiling temperature drift during processing and use. In addition, when an azeotrope is used as a solvent, the properties of the solvent remain constant because the composition of the solvent does not change during boiling or reflux. Azeotropes that are used as solvents also can be recovered conveniently by distillation.

However, the identification of new, environmentally-safe, non-fractionating mixtures that are commercially useful is complicated due to the fact that azeotrope formation is not readily predictable. Therefore, industry is continually seeking new azeotrope and azeotrope-like mixtures. This invention satisfies these needs among others.

SUMMARY OF THE INVENTION

A heteroazeotrope-like composition has been found that consists essentially of 1,1,2,3-tetrachloropropene (TCP) and hydrogen fluoride (HF). This azeotrope-like composition is useful as a solvent in various applications, such as removing surface oxidation from metals. Moreover, this azeotrope-like composition is useful as an intermediate in the synthesis of certain hydrofluoroolefins, such as HFO-1234yf.

Accordingly, provided is an azeotrope-like composition consisting essentially of 1,1,2,3-tetrachloropropene and hydrogen fluoride.

In another aspect of the invention, provided is a method for forming an azeotropic or azeotrope-like composition comprising blending hydrogen fluoride with 1,1,2,3-tetrachloropropene at a temperature of from about 0° C. to about 60° C. and at a pressure of about 7 psia to about 58 psia to produce an azeotrope-like mixture consisting essentially of about 1 to about 95 weight percent hydrogen fluoride and from about 5 to about 99 weight percent 1,1,2,3-tetrachloropropene.

In yet another aspect of the invention, provided is a solvent comprising an azeotrope-like composition consisting essentially of 1,1,2,3-tetrachloropropene and hydrogen fluoride.

In another aspect of the invention, provided is a sprayable composition comprising an azeotrope-like composition consisting essentially of 1,1,2,3-tetrachloropropene and hydrogen fluoride.

And in other aspect of the invention, provided is a method for removing surface oxidation from a substrate comprising contacting an oxidized surface of a metal substrate with a solvent comprising the novel azeotrope-like compositions described herein under conditions effective to remove an amount of metal oxides from said surface

BRIEF DESCRIPTION OF THE DRAWINGS

FIG. 1 shows a plot of the vapor pressures of the mixtures formed in Example 2 as measured at 0, 25, and 60° C.

DETAILED DESCRIPTION OF THE PREFERRED EMBODIMENTS OF THE INVENTION

The present invention provides compositions which comprise hydrogen fluoride (HF) and 1,1,2,3-tetrachloropropene (TCP) in amounts effective to form an azeotrope-like composition, as well as methods involving such azeotrope-like compositions. In certain preferred embodiments, these azeotrope-like compositions are binary azeotropes which consist essentially of combinations of only hydrogen fluoride with TCP.

As used herein, the term "azeotrope-like" relates to compositions that are strictly azeotropic and/or that generally behave like azeotropic mixtures. An azeotropic mixture is a system of two or more components in which the liquid composition and vapor composition are equal at the stated pressure and temperature. In practice, this means that the components of an azeotropic mixture are constant-boiling or essentially constant-boiling and generally cannot be thermodynamically separated during a phase change. The vapor composition formed by boiling or evaporation of an azeotropic mixture is identical, or substantially identical, to the original liquid composition. Thus, the concentration of components in the liquid and vapor phases of azeotrope-like compositions change only minimally, if at all, as the composition boils or otherwise evaporates. In contrast, boiling or evaporating non-azeotropic mixtures changes the component concentrations in the liquid phase to a significant degree.

As used herein, the terms "heteroazeotrope" and "heterogeneous azeotrope" mean an azeotrope-like composition comprising a vapor phase concurrently with two liquid phases.

As used herein, the term "consisting essentially of", with respect to the components of an azeotrope-like composition, means the composition contains the indicated components in an azeotrope-like ratio, and may contain additional components provided that the additional components do not form new azeotrope-like systems. For example, azeotrope-like mixtures consisting essentially of two compounds are those that form binary azeotropes, which optionally may include one or more additional components, provided that the additional components do not render the mixture non-azeotropic and do not form an azeotrope with either or both of the compounds (e.g., do not form a ternary azeotrope).

The term "effective amounts" as used herein refers to the amount of each component which, upon combination with the other component, results in the formation of an azeotrope-like composition of the present invention.

The term "dispensed form" as used herein refers to a physical form of a fluid as it is spread, distributed, and/or diffused over an area or through a volume. Examples of dispensed forms include aerosols and sprays.

In certain preferred embodiments, the azeotrope-like composition contains from about 1 to about 95 weight percent HF and from about 5 to about 99 weight percent TCP, more preferably from about 5 weight percent to about 95 weight percent HF and from about 5 weight percent to about 95 weight percent TCP, most preferably from about 55 weight percent to about 95 weight percent HF and from about 5 weight percent to about 45 weight percent TCP.

The composition of the present invention preferably has a boiling point of from about 0° C. to about 60° C. at a pressure from about 7 psia to about 58 psia. For example, a preferred azeotrope-like composition consists essentially of about 95±2 weight percent HF and about 9±2 weight percent TCP and has a normal boiling point of about 23° C.

The azeotrope-like compositions of the present invention can be produced by combining effective amounts of TCP with HF. Any of a wide variety of methods known in the art for combining two or more components to form a composition can be adapted for use in the present methods. For example, TCP and HF can be mixed, blended, or otherwise combined by hand and/or by machine, as part of a batch or continuous reaction and/or process, or via combinations of two or more such steps. In light of the disclosure herein, those of skill in the art will be readily able to prepare azeotrope-like compositions according to the present invention without undue experimentation.

In another embodiment of the invention, the azeotrope-like compositions described herein can be used as a solvent, particularly a cleaning solvent. In certain embodiments, the solvent is contacted with an oxidized surface of a metal substrate to remove or reduce at least a potion of the oxidized surface. Such solvents may be applied to the targeted substrate via any means known in the art, such as dipping, spraying, wiping, and the like.

In certain preferred embodiments, provided is a sprayable composition comprising the novel azeotrope-like compositions described herein. In certain embodiments, the sprayable composition is an aerosol. In certain the sprayable composition further comprises other components such as inert ingredients, co-solvents, propellants, co-propellants, and the like.

In certain embodiments, the novel azeotrope-like compositions described herein are useful intermediates derived from during synthesis of certain hydrofluoroolefins, such as 2,3,3,3-tetrafluoropropene (HFO-1234yf). For example, where TCP and HF are introduced into a reactor during a HFO-1234yf synthesis reaction, at least a portion of these components form an azeotrope which subsequently can be recovered from the associated reaction product stream.

In certain embodiments, method for reducing the boiling point of a hydrochloropropane is provided wherein the method comprises blending effective amounts of TCP and HF to form an azeotrope-like mixture consisting essentially of TCP and HF. Lowering the boiling point of TCP is advantageous when the TCP is used as a reactant in a vapor phase fluorination reaction. More particularly, lowering the boiling point facilitates vaporization of the compound and, thus, helps prevent decomposition of the compound and also reduces the amount of energy required by the fluorination process.

Accordingly, also provided is a method for fluorinating an organic compound comprising (a) providing an azeotrope-like composition consisting essentially of TCP and HF; and (b) reacting at least a portion of said TCP in the vapor phase with a fluorinating agent to produce at least one fluorinated organic compound, preferably a hydrofluoroolefin, more preferably a tetrafluoropropene, and even more preferably a 2,3,3,3-tetrafluoropropene.

EXAMPLES

The invention is further illustrated in the following example which is intended to be illustrative, but not limiting in any manner.

Example 1

Approximately 9 g of 1,1,2,3-tetrachloropropene (TCP) was blended in 91 g of HF to at about 25° C. and about 14.6 psia. The formation of a heterogeneous azeotrope-like composition was observed.

Example 2

TCP and HF were blended to form heterogeneous azeotrope mixtures at different compositions. The vapor pressures of the mixtures are measured at about 0, 25, and 60° C. The results of these measurements are provided in Table 1.

TABLE 1

P-T-X of TCP/HF System.

| | Pressure (Psia) | | |
|---|---|---|---|
| Wt. % HF | T = 0° C. | T = 25° C. | T = 60° C. |
| 0.00 | 0.0 | 0.1 | 0.24 |
| 8.70 | 6.71 | 17.64 | 51.81 |
| 14.58 | 7.48 | 18.57 | 51.95 |
| 19.59 | 8.16 | 19.34 | 52.10 |
| 24.14 | 8.75 | 19.93 | 53.75 |
| 28.55 | 8.94 | 20.17 | 54.63 |
| 35.25 | 9.19 | 20.61 | 55.02 |
| 42.09 | 9.19 | 20.61 | 55.74 |
| 47.61 | 9.19 | 20.61 | 55.94 |
| 52.18 | 9.38 | 21.00 | 56.28 |
| 55.06 | 9.96 | 21.63 | 57.25 |
| 66.41 | 8.89 | 20.31 | 56.28 |
| 74.89 | 6.95 | 17.84 | 54.72 |
| 100.0 | 6.87 | 17.82 | 52.43 |

The data in Table 1 demonstrates that these mixtures exhibit azeotrope-like characteristics since the vapor pressures of mixtures of TCP and HF are higher, at all indicated blend proportions, than TCP and HF alone, i.e. as indicated in the first and last rows when HF is 0.0 wt. % and TCP is at 100.0 wt % as well as when TCP is at 0.0 wt. % and HF is at 100.0 wt. %.

The data from Table 1 is depicted graphically in FIG. 1.

Example 3

This example demonstrates the azeotropic-like properties of TCP/HF mixtures via Vapor-Liquid—Liquid Equilibrium (VLLE).

Approximately 14.4 g of 1,1,2,3-tetrachloropropene (TCP) was blended with 15.7 g of HF to form, upon visual observation, a heterogeneous mixture at 23° C. A second mixture of 53 wt % TCP and 47 wt % HF was prepared. The vapor compositions of the two mixtures were sampled at room temperature of 23° C. The result shows that the weight percent of HF in the vapor of mixture 1 is 90.9, and the weight percent of HF in the vapor of mixture 2 is 91.5. Accordingly, an azeotrope-like composition was formed having about 91±2 wt. % HF at 23° C.

What is claimed is:
1. An azeotrope-like composition consisting essentially of 1,1,2,3-tetrachloropropene and hydrogen fluoride.
2. The azeotrope-like composition of claim 1, wherein said azeotrope-like composition consists essentially of from about 1 to about 95 weight percent hydrogen fluoride and from about 5 to about 99 weight percent 1,1,2,3-tetrachloropropene.

3. The azeotrope-like composition of claim 2, wherein said azeotrope-like composition has a boiling point of from about 0° C. to about 60° C. at a pressure of from about 7 psia to about 58 psia.

4. The azeotrope-like composition of claim 1, wherein said azeotrope-like composition consists of hydrogen fluoride and 1,1,2,3-tetrachloropropene.

5. The azeotrope-like composition of claim 4 wherein the hydrogen fluoride in present in an amount of from about 1 to about 95 weight percent and from about 5 to about 99 weight percent 1,1,2,3-tetrachloropropene.

6. The azeotrope-like composition of claim 5 wherein the hydrogen fluoride in present in an amount of from about 5 to about 91 weight percent and from about 9 to about 95 weight percent 1,1,2,3-tetrachloropropene.

7. The azeotrope-like composition of claim 6 wherein the hydrogen fluoride in present in an amount of from about 55 to about 89 weight percent and about 11 to about 45 weight percent 1,1,2,3-tetrachloropropene.

8. A method for forming an azeotropic or azeotrope-like composition comprising blending hydrogen fluoride with 1,1,2,3-tetrachloropropene at a temperature of from about 0° C. to about 60° C. and at a pressure of about 7 psia to about 58 psia to produce an azeotrope-like mixture consisting essentially of about 1 to about 95 weight percent hydrogen fluoride and from about 5 to about 99 weight percent 1,1,2,3-tetrachloropropene.

9. The method of claim 8 wherein said azeotrope-like mixture consists of about 1 to about 95 weight percent hydrogen fluoride and from about 5 to about 99 weight percent 1,1,2,3-tetrachloropropene.

10. The method of claim 9 wherein said azeotrope-like mixture has from about 5 to about 91 weight percent hydrogen fluoride and from about 9 to about 95 weight percent 1,1,2,3-tetrachloropropene.

11. The method of claim 9 wherein azeotrope-like mixture has from about 55 to about 89 weight percent hydrogen fluoride and about 11 to about 45 weight percent 1,1,2,3-tetrachloropropene.

12. A solvent comprising an azeotrope-like composition according to claim 1.

13. The solvent of claim 12 having at least about 50 weight percent of said azeotrope-like composition.

14. The solvent of claim 12 having at least about 95 weight percent of said azeotrope-like composition.

15. The solvent of claim 12 consisting essentially of said azeotrope-like composition.

16. The solvent of claim 12 consisting of said azeotrope-like composition.

17. A sprayable composition comprising an azeotrope-like composition according to claim 1.

18. The sprayable composition of claim 17 having at least about 50 weight percent of said azeotrope-like composition.

19. The sprayable composition of claim 17 having at least about 95 weight percent of said azeotrope-like composition.

20. The sprayable composition of claim 17 consisting essentially of said azeotrope-like composition.

21. The sprayable composition of claim 17 consisting of said azeotrope-like composition.

22. A method for removing surface oxidation from a substrate comprising contacting an oxidized surface of a metal substrate with a solvent according to claim 12 under conditions effective to remove an amount of metal oxides from said surface.

* * * * *